United States Patent [19]

Orlando

[11] Patent Number: 4,568,426

[45] Date of Patent: Feb. 4, 1986

[54] CONTROLLED ATMOSPHERE OVEN

[75] Inventor: Thomas W. Orlando, San Antonio, Tex.

[73] Assignee: Alcor, Inc., San Antonio, Tex.

[21] Appl. No.: 465,109

[22] Filed: Feb. 9, 1983

[51] Int. Cl.[4] .......................... B01D 3/42; F27B 5/00; G01N 31/12
[52] U.S. Cl. ........................................ 203/1; 208/128; 219/390; 422/78; 422/80; 436/155; 202/208
[58] Field of Search .............................. 422/78, 79, 80; 436/155, 157, 139.2; 219/390; 373/110; 203/1; 201/1; 208/125, 128, 132, 106; 202/208, 215, 23.1; 196/120, 121

[56] References Cited

U.S. PATENT DOCUMENTS

| | | | |
|---|---|---|---|
| 3,186,801 | 6/1965 | Hampton | 422/80 |
| 3,475,131 | 10/1969 | Kevlemans | 422/80 |
| 3,694,157 | 9/1972 | Koch et al. | 436/155 |
| 3,864,088 | 2/1975 | Delin et al. | 422/80 |
| 4,351,801 | 9/1982 | Bartke | 436/155 |
| 4,375,027 | 2/1983 | Zeto et al. | 219/390 |

FOREIGN PATENT DOCUMENTS

WO80/01108 5/1980 PCT Int'l Appl. .................... 422/80

OTHER PUBLICATIONS

Dec. 9, 1981–General concept of applicant's Controlled Atmosphere Oven, disclosed at National Meeting of ASTM, in Phoenix, Arizona.
Aug. 1980–Publication of article entitled *An Alternative to the Conradson Carbon Residue Test*, by Fern Noel.
Ultra-Mat II, porcelain furnace developed by Unitek Corporation (advertisement).
Retort, developed by Lindberg G. S. (advertisement).
Rapid Temp KBL Oven, developed by CM, Inc. (advertisement).
DSC-4 Calorimeter, developed by Perkin-Elmer Corp. (advertisement).
Isotemp Furnace, developed by Fisher Scientific Company (advertisement).

*Primary Examiner*—S. Leon Bashore
*Assistant Examiner*—K. M. Hastings
*Attorney, Agent, or Firm*—Gunn, Lee & Jackson

[57] ABSTRACT

An oven for heating a distillable material in a preselected gas atmosphere. The oven comprises an inner heating chamber adapted to receive a spherical gravity lid, the heating chamber being connected to and in communication with a gas exhaust tube having a condensate trap at the termination thereof. The inner heating chamber is also in communication with and surrounded by an outer gas flow chamber, the outer gas flow chamber having a plurality of heater elements therein. The gas exhaust tube is surrounded by an ante chamber which is in communication with the outer chamber. The heater elements are continuously monitored by a programmable controller and a thermocouple in communication therewith. During oven operation, a purge gas is introduced to the ante chamber and flows therefrom into the outer gas flow chamber around the heater elements and into the top of the inner heating chamber. The lighter purge gas initially displaces the denser oxygen within the inner heating chamber and urges it outward through the gas exhaust tube and an exhaust chimney connected thereto. During the heating phase, the preselected purge gas continuously purges the inner heating chamber of volatile gas from the heated distillable material. As the denser material gas is urged outward through the gas exhaust tube by the warm purge gas, the cool purge gas entering the ante chamber causes the material gas within the exhaust tube to condense therein and be collected in the condensate trap.

12 Claims, 12 Drawing Figures

CONTROLLED ATMOSPHERE OVEN

BACKGROUND OF THE INVENTION

Determining the coke forming tendency of petroleum products frequently involves the use of the Conradson Carbon Residue test. The Conradson Carbon Residue (CCR) test is designed to indicate the extent of coke that a petroleum product will form under thermal degradation conditions, such as might be encountered in distillation towers, heat exchangers, and reactors. Since its inception, the CCR test has been applied to characterize a multitude of petroleum products and is currently defined by ASTM D 189-76 and IP 13/66.

Despite the popularity of this widely used standard, there are disadvantages to the CCR test. For example, the test is generally slow, lacks precision, and requires the utilization of large samples (5-10 grams). Due to the utilization of an open flame and the resultant smoke, the CCR test is also hazardous and messy.

In light of these shortcomings, work was undertaken by Fern Noel of Imperial Oil Ltd., Canada, to develop a procedure or method which would duplicate the results of the CCR test, but overcome the disadvantages thereof. The easier, more precise, and faster method developed by Fern Noel for obtaining the same results as the CCR test was set forth in an article entitled *An Alternative To The Conradson Carbon Residue Test*, the disclosure of which is incorporated by reference. The method and results described therein had initially been disclosed by Noel at a meeting of the American Chemical Society (ACS) in Las Vegas in August of 1980 and copies of Noel's presentation were made available at that time.

Under the standard CCR procedure, there is no purge of the system with an inert gas, such as nitrogen, at any time during the test. However, the results of Noel's experiments indicated that the presence of trace amounts of oxygen during the early stages of coking caused the formation of slightly more coke. Nevertheless, Noel's object was to produce results equivalent to CCR values regardless of this effect.

Noel determined that coke values similar to the CCR test values could be obtained using conditions and equipment other than that defined by the American Society of Testing Materials (ASTM). Noel's results prescribed the following conditions for optimum correlation with the CCR test:

1. Temperature of 500° C. ±10° C.
2. Coking time not less than 20 minutes.
3. Nitrogen blanketing.
4. Heating rates of (2° to 40° C./min) up to coking temperature of 500° C.
5. Sample container should be glass.
6. Glass cups of 3×1 cm can be used for sample sizes of 30-100 mg. For smaller samples, sample cups should be decreased in size to avoid the thin film effect.

Using the basic groundwork of Noel's work, the assignee of the present invention began development of a single unit tester oven that would provide all the advantages of the new method. The development of the present invention was assisted by the coincidental market introduction of a programmable controller by the Barber-Colman Co., Model 570. Nevertheless, the invention oven may utilize any one of several possible heat control means and is designed to achieve any type of small scale batch heating of liquids or solids in an ambient pressure gas atmosphere.

The present invention achieves the advantages of Noel's new carbon residue testing method by providing an oven wherein a petroleum product may be heated in a preselected gas atmosphere. The oven comprises an inner heating chamber having a cylindrical wall with a plurality of purge gas inlet ports therethrough near a top opening thereof and a bottom floor having a gas outlet port therethrough. The gas outlet port permits the passage of purged oxygen and petroleum gas from the inner heating chamber into a gas exhaust tube during the purging phase and heating phase, respectively. The top opening of the inner heating chamber permits the introduction of the petroleum product into the heating chamber, the top of which has a chamfered edge for receiving thereon a spherical gravity lid. The inner heating chamber and gas exhaust tube are surrounded by an outer gas flow chamber and an ante chamber, respectively, the outer gas flow chamber being in communication with the ante chamber and having a plurality of concealed heater elements therein contiguous to the outer wall of the inner heating chamber. The heater elements are continuously monitored by a programmable external controller which is in communication with a thermocouple protruding through the inner wall of the inner heating chamber, thereby permitting the product within the sealed inner heating chamber to be heated evenly at the rate and temperature desired.

During the operation of the oven, a glass vial containing the liquid or solid product to be heated is introduced to the inner heating chamber and subsequently sealed therein by the gravity lid. A preselected inert or reactive purge gas is thereafter introduced to the ante chamber and flows therefrom into the outer gas flow chamber around the heater elements and into the inner heating chamber through the gas inlet ports. The lighter purge gas initially purges the inner heating chamber of oxygen by gradually urging the denser air through the gas outlet port into the gas exhaust tube. After the inner heating chamber has been sufficiently purged, the product is heated at the rate and temperature specified by the controller program. Throughout the heating phase, the lighter purge gas continues to purge the inner heating chamber of volatile vapor or gas by urging the denser vapor through the gas outlet port and gas exhaust tube. The cool purge gas entering the oven through the ante chamber cools the gas outlet port resulting in a cooler surface that causes much of the vapor within the gas exhaust tube to condense therein. The condensed product is thereafter collected in a condensate trap connected to the bottom of the oven at the termination of the gas exhaust tube. The oxygen and process or product vapor that does not condense is properly removed from the oven through an exhaust chimney which is connected to the gas exhaust tube and in communication with an exhaust hood.

BRIEF DESCRIPTION OF THE PRIOR ART

The original oven developed by Imperial Oil Ltd. for implementation of Noel's method is the most relevant prior art known to applicant. The Imperial oven permits the introduction of various purge gases and does not expose the heater elements to the petroleum product. Nevertheless, it is readily distinguishable from the present invention. For example, the Imperial Oil oven is purged by forcing the purge gas through the heating chamber. Furthermore, the Imperial Oil oven utilizes a bolted lid, thereby creating prime conditions for a subsequent explosion, and a crude, resistance furnace. The Imperial oven does not teach the use of a gravity seal lid, a programmable controller, or an outer gas flow chamber having heater elements therein and permitting the flow of purge gas therethrough. Unlike the compact, uniform temperature heating chamber of the present invention, the Imperial Oil oven utilizes hot and cool zones into which the test material is introduced by means of a movable tube which is inserted into the heating chamber. Finally, in the Imperial Oil oven, the thermocouple is located on the tip of the movable tube in the center of the heating chamber rather than on the inner wall of the heating chamber, as disclosed in the present invention. Placement of the thermocouple away from the wall creates an important temperature variation and lag situation. The variation is due to the time lag between the heating and the time it takes for the thermocouple to sense the heat. The farther away from the heat source the sensor is, the more time lag will occur resulting in wide temperature cycling.

SUMMARY OF THE INVENTION

It is a primary object of the present invention to provide an oven wherein a material may be heated in a preselected gas atmosphere.

It is another object of the present invention to provide an oven wherein air and material gas are continuously displaced therefrom by the introduction of a lighter purge gas into the heating chamber.

It is still another object of the present invention to provide an oven wherein the heater elements are exterior to and concealed from the heating chamber.

It is a further object of the present invention to provide an oven wherein the heating chamber is adapted to receive thereon a spherical gravity lid for sealing the opening thereof.

It is a still further object of the present invention to provide an oven wherein the gas of the heated material is purged from the heating chamber and thereafter condensed and collected.

It is yet a further object of the present invention to provide an oven wherein a material may be evenly heated at a constant or uniformly changing temperature.

It is yet a still further object of the present invention to provide a method for heating a material in preselected gas atmosphere utilizing the invention oven as described herein.

These and other objects as well are achieved in the present invention by providing an oven wherein a petroleum product or other distillable material may be heated in a preselected gas atmosphere. The oven comprises an inner heating chamber having a cylindrical wall with a plurality of purge gas inlet ports therethrough near a top opening thereof and a bottom floor having a central gas outlet port therethrough. The gas outlet port permits the passage of oxygen and volatile product vapor from the inner heating chamber into a gas exhaust tube, which is connected to the bottom floor of the inner heating chamber. The gas exhaust tube permits the flow of oxygen and product gas during the purging and heating phase, respectively, into an exhaust chimney or a condensate trap connected to the gas exhaust tube at the termination thereof. The top opening of the inner heating chamber is of sufficient size to permit the introduction of one or more glass vials containing the petroleum product into the inner heating chamber. The inner heating chamber has a chamfered edge on the top thereof for receiving a spherical gravity lid thereon. The gravity lid provides a tight seal for the inner heating chamber while maintaining an explosion safe environment therein. The inner heating chamber and gas exhaust tube are surrounded by an outer gas flow chamber and an ante chamber, respectively, the outer gas flow chamber being in communication with the ante chamber. The outer gas flow chamber is sealed by a flange extending from the top of the inner heating chamber and has a plurality of concealed heater elements therein contiguous to the outer wall of the inner heating chamber. The resistance heater elements are continuously monitored by an external programmable controller which is in communication with a thermocouple protruding through the inner wall of the inner heating chamber, thereby permitting the product sample within the sealed inner heating chamber to be heated evenly at the rate and temperature desired. The oven is preferably housed within a cabinet having a thermal barrier therein separating the sensitive controller from the heating and purging elements of the invention.

During the operation of the oven, the preweighed distillable material is introduced to the inner heating chamber and sealed therein by the spherical gravity lid. The inner heating chamber is thereafter purged of oxygen by the introduction of a preselected inert or reactive purge gas from an external gas supply. The purge gas enters the ante chamber through a purge gas feed line and flows therefrom into the outer gas flow chamber. Within the outer gas flow chamber, the purge gas continuously bathes the heater elements therein and subsequently flows therefrom into the top of the inner heating chamber through the purge gas inlet ports. The lighter purge gas gradually displaces the oxygen within the inner heating chamber by urging the denser oxygen outward through the gas outlet port and gas exhaust tube.

After the inner heating chamber is thoroughly purged of oxygen, the concealed heater elements heat the walls of the inner heating chamber, thereby heating the distillable material therein. Throughout the heating phase, the preselected purge gas continuously bathes the heater elements within the outer gas flow chamber and displaces the volatile product gas within the inner heating chamber. This is accomplished by the warm purge gas entering the top of the inner heating chamber continuously urging the denser product gas outward through the gas outlet port and gas exhaust tube.

As the cool purge is continuously introduced to the oven through the ante chamber surrounding the top portion of the gas exhaust tube, the purged product gas is caused to condense therein and be received by the condensate trap, thereby reducing unnecessary discharge of the hazardous gas. The oxygen and product gas which is not condensed flows outward from the system through an exhaust chimney connected to the gas exhaust tube intermediate to the ante chamber and condensate trap.

At the conclusion of the heating phase, heating is discontinued, the inner heating chamber is cooled, the gravity lid is removed, and the test material is removed and reweighed to determine its weight loss. The cooling process is assisted by the continuous flow of purge gas around the heater elements into the inner heating chamber. The utilization of a programmable controller permits the controlled heating of the petroleum product and the controlled purging of the inner heating chamber at a high or low flow rate, the heating and purging being determined by the oven operator and the parameters of the test.

DETAILED DESCRIPTION OF THE PREFERRED EMBODIMENT

Figure 1:
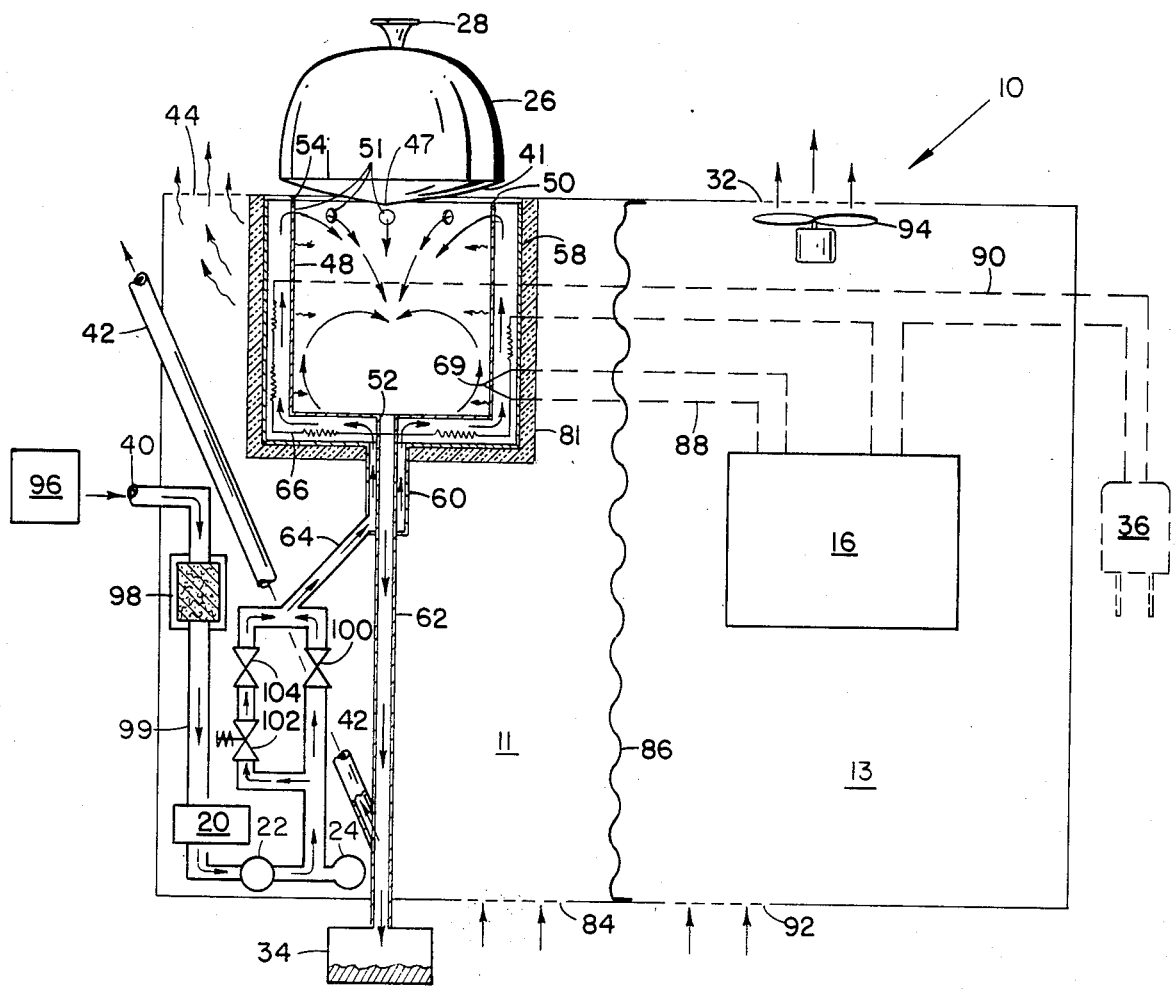
FIG. 1 is a schematic diagram of the oven heating system and gas flow system.

Referring to FIG. 1, the invention oven is identified by the number 10. The oven 10 generally comprises a test chamber 11 housing the heating and gas flow portions of the system and a control chamber 13 housing the programmable controller 16. The controller 16 monitors the continuous purging of inner heating chamber 48 by a preselected gas and the controlled heating of a distillable material 105 by heater elements 66. The oven 10 is designed to heat a material 105 in a thoroughly purged, hot chamber at a constant or uniformly changing temperature. The controlled atmosphere within heating chamber 48 is basically achieved by introducing a lighter, preselected gas into the top thereof and allowing the lighter gas to gradually displace the denser air or material vapor within the chamber 48.

As illustrated in FIG. 7–FIG. 10, the various elements of the oven 10 described hereinbelow are preferably housed in a stainless steel cabinet 12 supported by a plurality of legs 14. The cabinet or outer housing 12 comprises a front instrumentation panel 12a, a top panel 12b, a bottom panel 12c, a rear access panel 12d, and a pair of opposed side panels 12e. The front instrumentation panel 12a comprises the input unit of the microprocessor based controller 16, an ON/OFF power switch 18, a dual function purge gas pressure switch 20, a purge gas ON/OFF valve 22, and a purge gas pressure gauge 24. Located on the top panel 12b of oven 10 is a removable insulated gravity seal lid 26 having a lid handle 28 secured thereto and a lid rest 30 surrounding a plurality of control chamber outlet ports 32 which extend through top panel 12b. The bottom panel 12c of oven 10 comprises a plurality of test chamber inlet ports 84 and a plurality of control chamber inlet ports 92. A removable glass condensate trap 34 is secured to a condensate cap 35 which is connected to the bottom panel 12c of oven 10. The legs 14 connected to bottom panel 12c permit access to the condensate trap 34 for purposes of trap removal and proper disposal of the material collected therein.

The rear access panel 12d of oven 10 preferably comprises a power supply line 36, fuses 38, purge gas inlet orifice 40, exhaust chimney 42, and a plurality of test chamber outlet ports 44. The power supply line 36 is preferably in communication with an appropriate power supply, depending upon the option preselected by the user. The exhaust chimney 42 preferably terminates in close proximity to an exhaust hood (not shown). Access to the internal elements of the oven 10 is obtained by the easy removal of the rear panel 12d. Within the cabinet 12, a thermal barrier 86 separates the hot test chamber 11 which houses the inner heating chamber 48 from the control chamber 13 which houses the sensitive controller 16.

Figure 5:
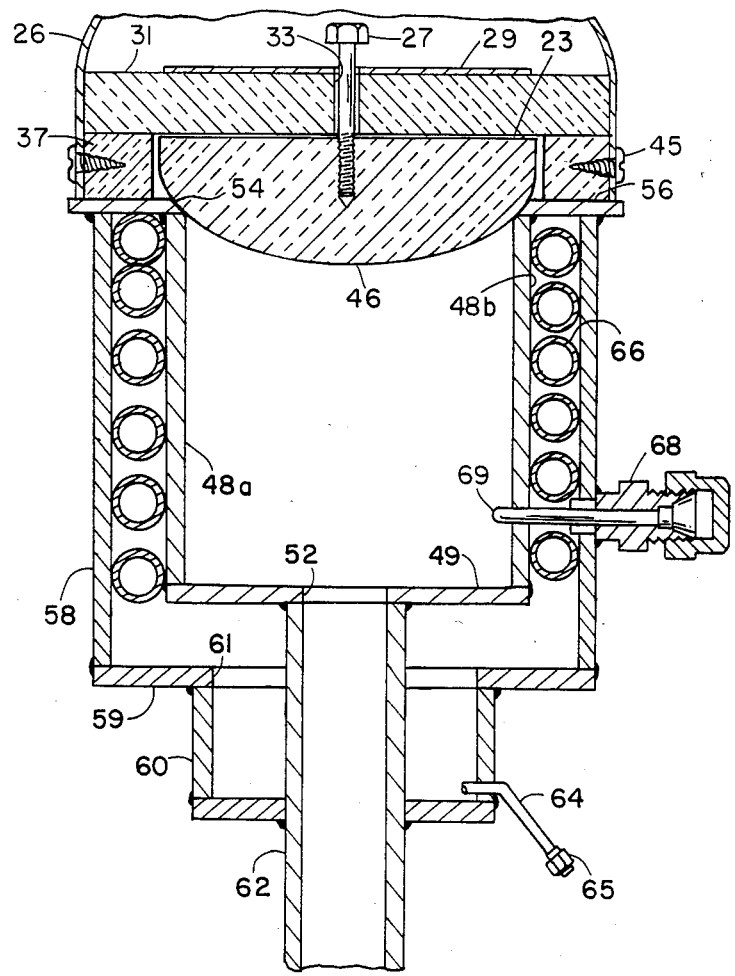
FIG. 5 is a cross-sectional view of the inner heating chamber, outer gas flow chamber, heater elements, gas exhaust tube, ante chamber, and gravity seal lid.
Figure 12:
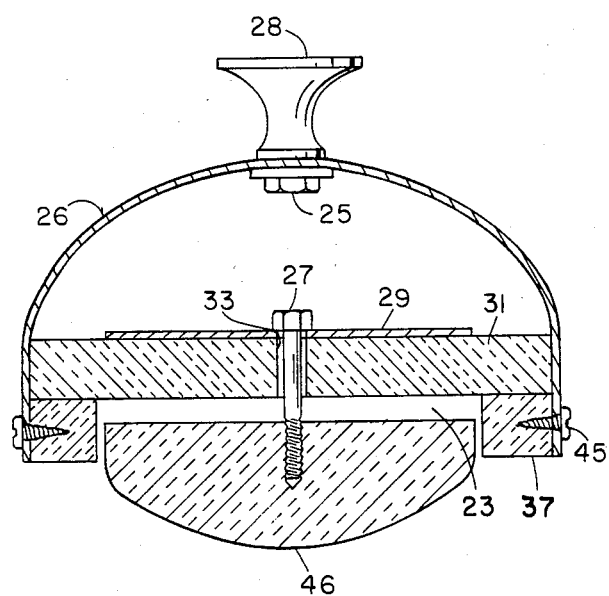
FIG. 12 is a cross-sectional view of the preferred gravity seal lid utilized in the invention oven.

As illustrated in FIG. 1, FIG. 5, and FIG. 12, the gravity seal lid 26 may have either a spherical bottom 41 or a spherical seal 46 which covers the top opening 50 of a cylindrical inner heating chamber 48. Spherical bottom 41 forms an integral unit with lid 26, as illustrated in FIG. 1, whereas spherical gravity seal 46 is a distinct solid element connected to lid 26 by a seal screw 27, as illustrated in FIG. 5 and FIG. 12. Spherical bottom 41 and spherical gravity seal 46 may also have a pointed tip 47, as illustrated in FIG. 1, to assist in the removal of condensation therefrom.

Spherical gravity seal 46, as illustrated in FIG. 5 and FIG. 12, is firmly secured to lid 26 by a moveable seal screw 27 which is inserted through the orifice 33 extending through steel plate 29 and an upper layer of ceramic insulation 31. Ceramic insulation layer 31 is appropriately connected to a lower layer of ceramic insulation 37. The moveable screw 27 permits the solid stainless steel seal 46 to float when it rests on the chamfered edge 54 of inner heating chamber 48. As illustrated in FIG. 5, the lower layer of ceramic insulation 37 is connected to lid 26 by a plurality of screws 45 and rests upon flange 56 when lid 26 is placed on inner heating chamber 48. Thus, the spherical seal 46 is suspended in a surrounding of ceramic insulation 31 and 37 with an air space 23 therebetween, thereby prohibiting condensation of vapor thereon. When the lid 26 is removed, as illustrated in FIG. 12, the head of moveable screw 27 becomes flush with the steel plate 29, which allows even weight distribution over the relatively weak ceramic layer 31.

Figure 3:
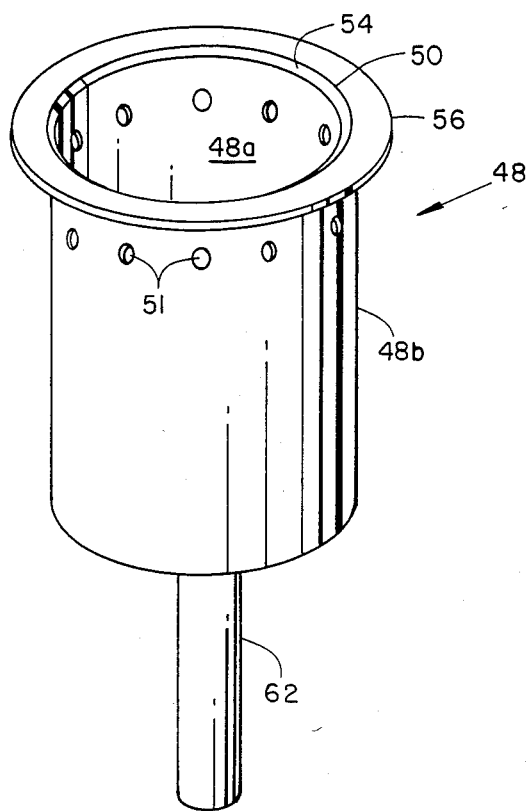
FIG. 3 is a perspective view of the inner heating chamber and gas exhaust tube.
Figure 4:
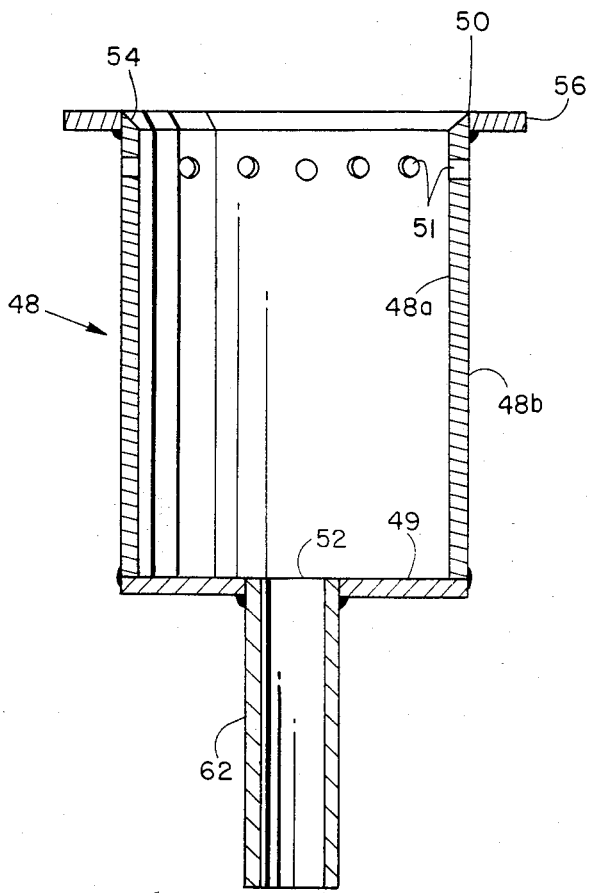
FIG. 4 is a cross-sectional view of the inner heating chamber and gas exhaust tube.

As illustrated in FIG. 3 and FIG. 4, the top of inner heating chamber 48 has a chamfered or angled edge 54 of approximately 45° for receiving floating spherical seal 46 or spherical bottom 41, thereby providing a tight, gravity seal of the top opening 50 of inner heating chamber 48. Due to the simple gravity seal, the lid 26 can be removed quickly and easily, thereby permitting ready access to inner heating chamber 48.

Cylindrical heating chamber 48 preferably comprises an inner wall 48a and outer wall 48b, a bottom or floor 49, and an outer cylindrical flange 56 surrounding the top opening 50 thereof. Inner heating chamber 48 is preferably constructed of stainless steel and preferably has a volume of approximately one liter. This size permits rapid and efficient heating and cooling and precise control thereof. The inner heating chamber 48 is further provided with a plurality of purge gas inlet ports 51 therethrough near top opening 50 thereof. The floor 49 is also provided with a centrally located purge gas outlet port 52 which provides communication between the inner heating chamber 48 and a gas exhaust tube 62, which is welded or otherwise connected to the floor 49 at the location of the purge gas outlet port 52.

As illustrated in FIG. 5, inner heating chamber 48 and gas exhaust tube 62 are surrounded by an outer gas flow chamber 58 and an ante chamber 60, respectively. Outer gas flow chamber 58 is sealed on the top thereof by the flange 56 of inner heating chamber 18. An opening 61 in the floor 59 of outer gas flow chamber 58 permits the flow of preselected purge gas from the ante chamber 60 into the outer gas flow chamber 58. Thus, the outer gas flow chamber 58 and ante chamber 60 may be considered as a single chamber surrounding inner heating chamber 48 and the top of gas exhaust tube 62. The purge gas is introduced to the ante chamber 60 through a gas feed line 64, which is appropriately connected to the remainder of the gas flow system by a gas feed line fitting 65.

Figure 6:
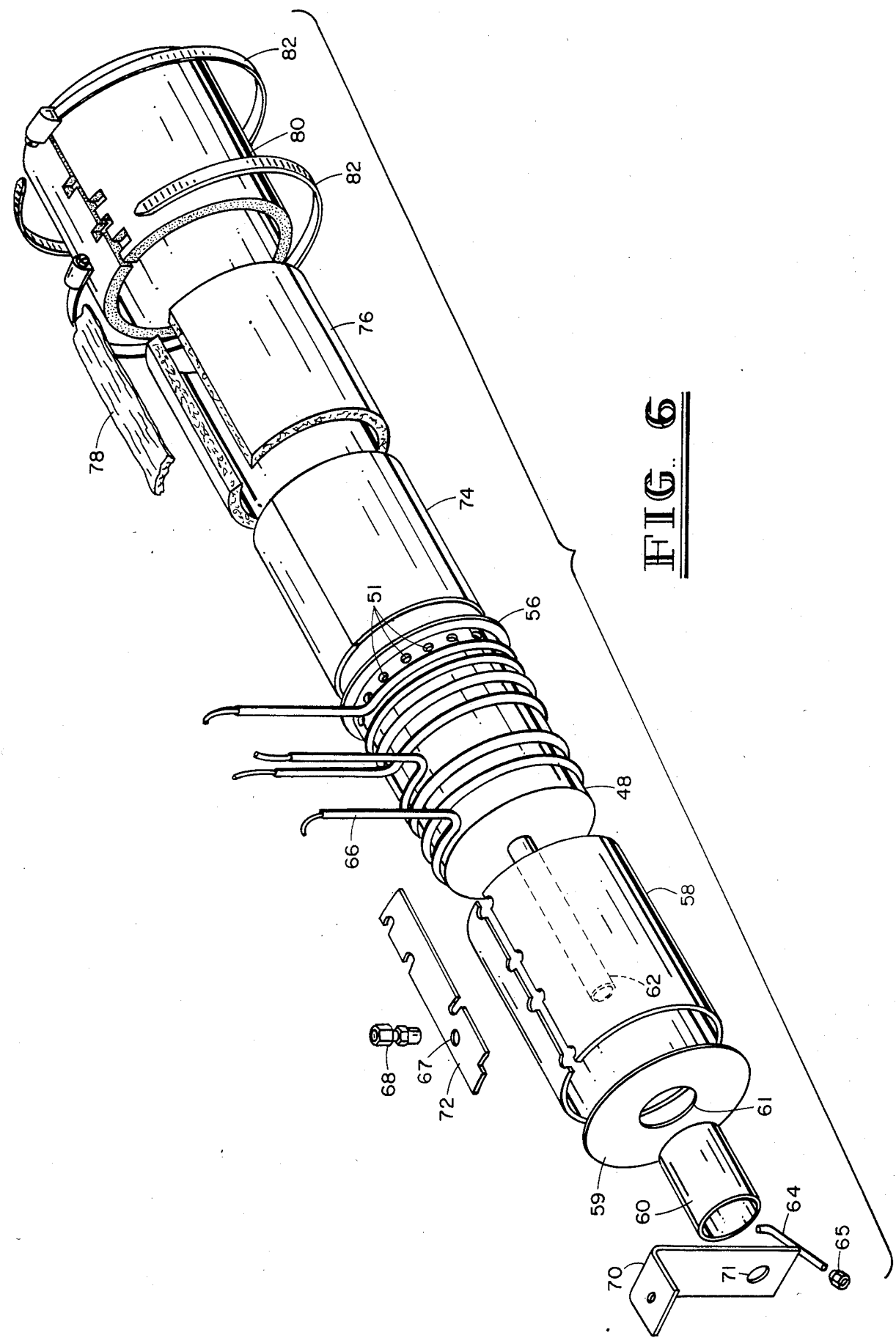
FIG. 6 is an exploded perspective view of the inner heating chamber, outer gas flow chamber, heater elements, gas exhaust tube, ante chamber, and heating chamber insulation.
Figure 7:
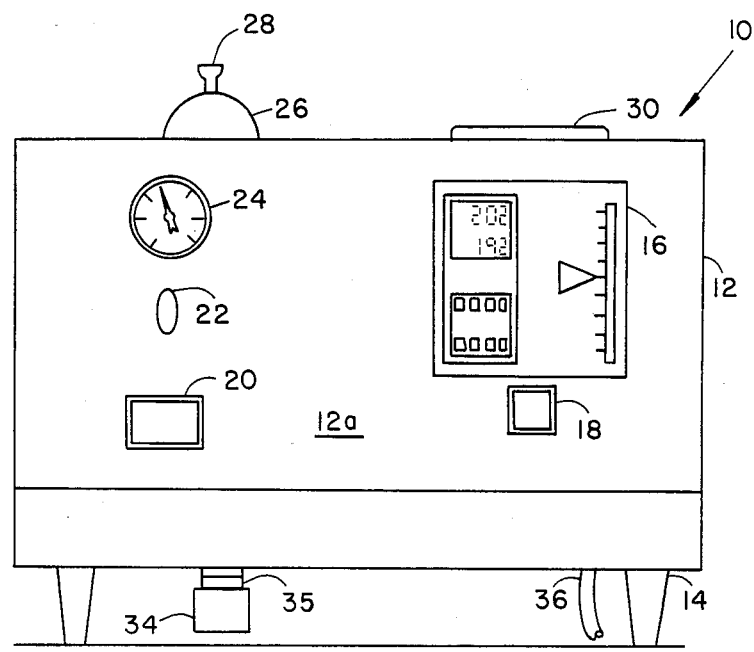
FIG. 7 is a front plan view of the cabinet housing the invention oven.
Figure 8:
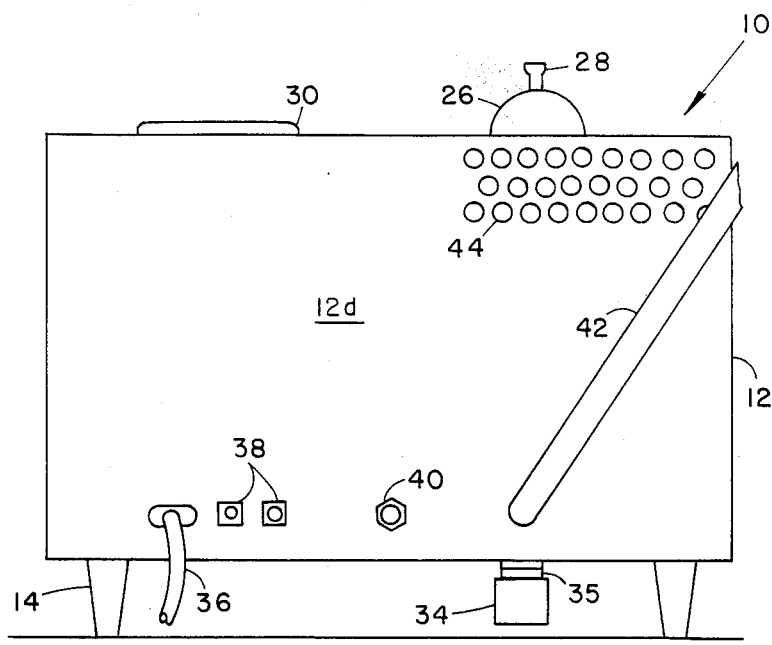
FIG. 8 is a rear plan view of the cabinet housing the invention oven.
Figure 9:
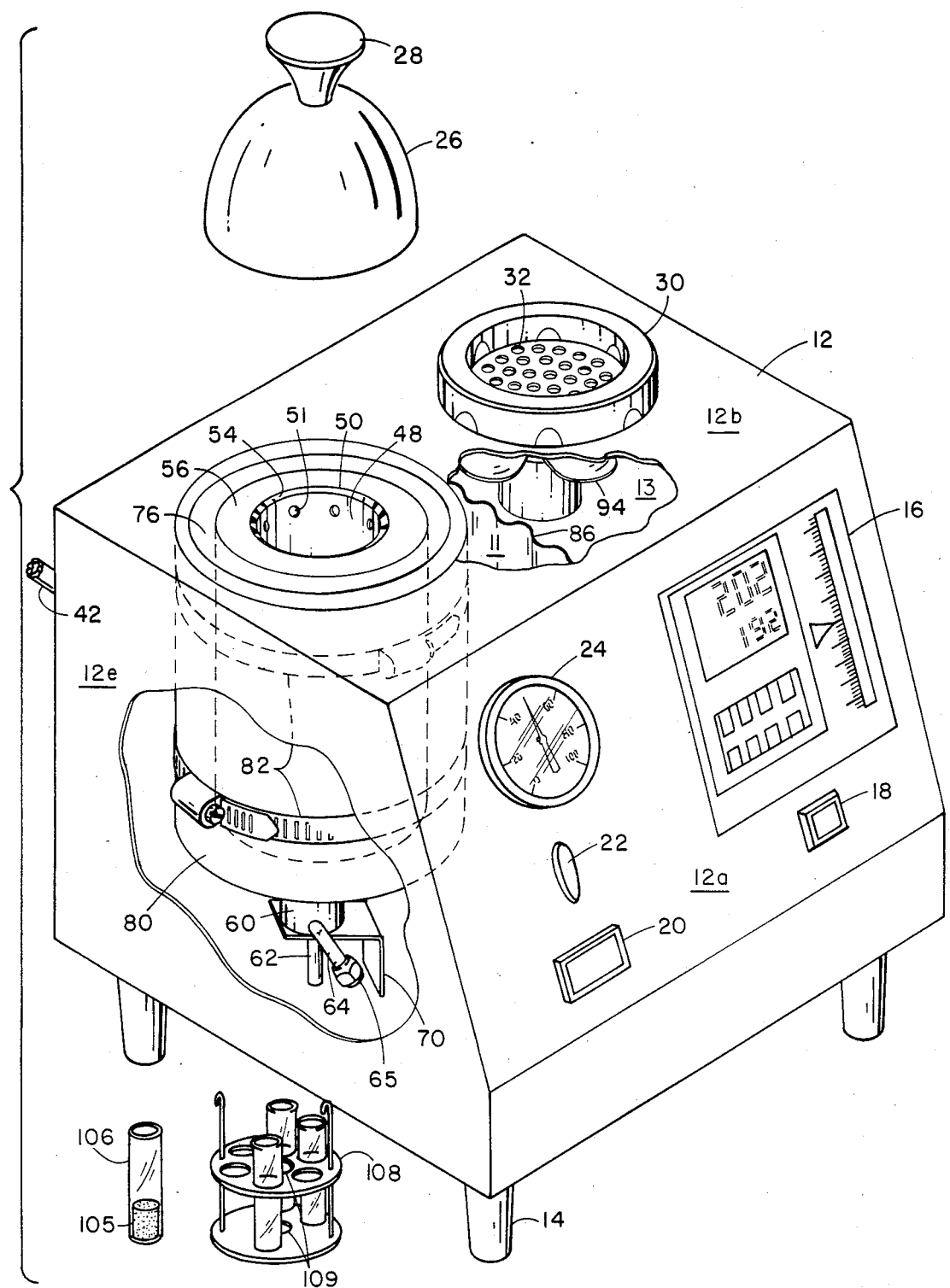
FIG. 9 is a perspective view of the oven cabinet and a transparent perspective view of the elements within the cabinet.
Figure 10:
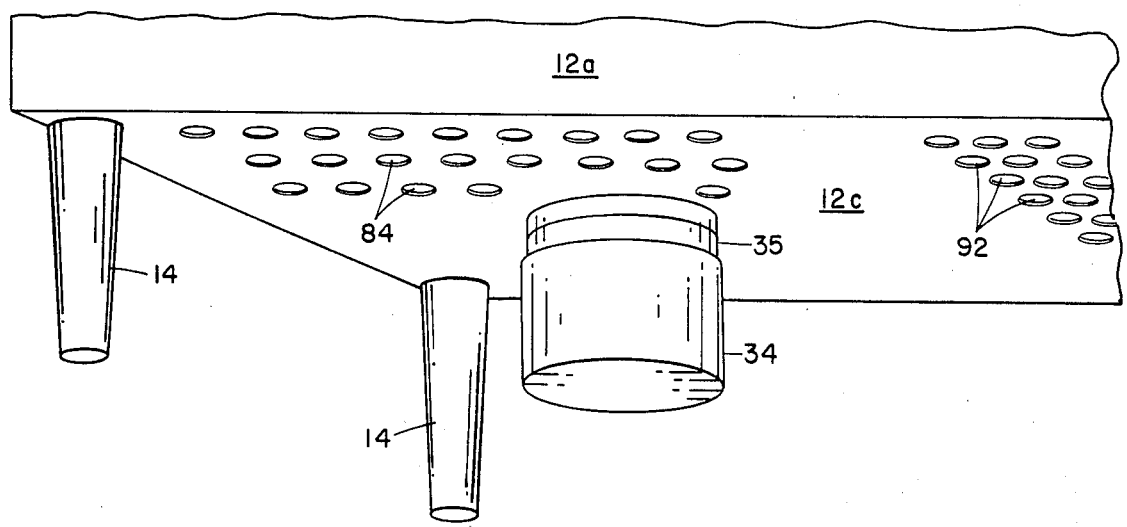
FIG. 10 is a bottom perspective view of the oven cabinet.

Located within the gas flow chamber 58 is a plurality of coiled resistance heater elements 66 contiguous to the outer wall 48b of inner heating chamber 48. As illustrated in FIG. 1, heater elements 66 are connected to the power supply line 36 and controller 16 by power leads 90. As illustrated in FIG. 6, heater elements 66 and preferably sealed within the chamber 58 by a patch plate 72 and the chamber 58 is provided with a thermocouple fitting 68 which is inserted through thermocouple orifice 67 in patch plate 72. As illustrated in FIG. 1 and FIG. 5, thermocouple fitting 68 permits the attachment of thermocouple leads 88 between the controller 16 and a thermocouple 69 which protrudes through the inner wall 48a of inner heating chamber 48. As illustrated in FIG. 6 and FIG. 9, the oven heating system is further provided with a grounding plate 70 which is connected to the bottom of the ante chamber 60 and has a grounding plate orifice 71 for receiving the gas exhaust tube 62 therethrough. The heater elements 66 are continuously monitored by the programmable controller 16 which is in communication with the thermocouple 69, the controller 16 thereby controlling the conduction heating of chamber walls 48a and 48b and the uniform convection heating of a petroleum product or other distillable material 105 within inner heating chamber 48.

Surrounding the outer gas flow chamber 58 is an inner layer of insulation paper 74, an intermediate insulation layer 76 comprising a fibrous blanket 78, and an outer insulation layer 80, as illustrated in FIG. 6. The insulation layers 74, 76, and 80 are adapted to permit communication between the heater elements 66, thermocouple 69, controller 16, and power supply line 36 and are secured to the outer gas flow chamber 58 by a pair of conventional clamps 82. It is to be understood, however, that any number of layers of numerous possible insulation materials, may be utilized. For example, the outer gas flow chamber 58 may be surrounded by a single layer of ceramic 81, as illustrated in FIG. 1. The test chamber 11 is also kept cool by the flow of ambient air into the cabinet 12 through test chamber inlet ports 84 and out of the cabinet 12 through test chamber outlet ports 44, as illustrated by the arrows in FIG. 1. The sensitive controller 16 is also protected from the heat within the test chamber 11 by the thermal barrier 86 and the flow of ambient air through the control chamber 13. The ambient air cooling the control chamber 13 enters through control chamber inlet ports 92 and is urged outward therefrom through control chamber outlet ports 32 by fan 94, as illustrated in FIG. 1.

Figure 2:
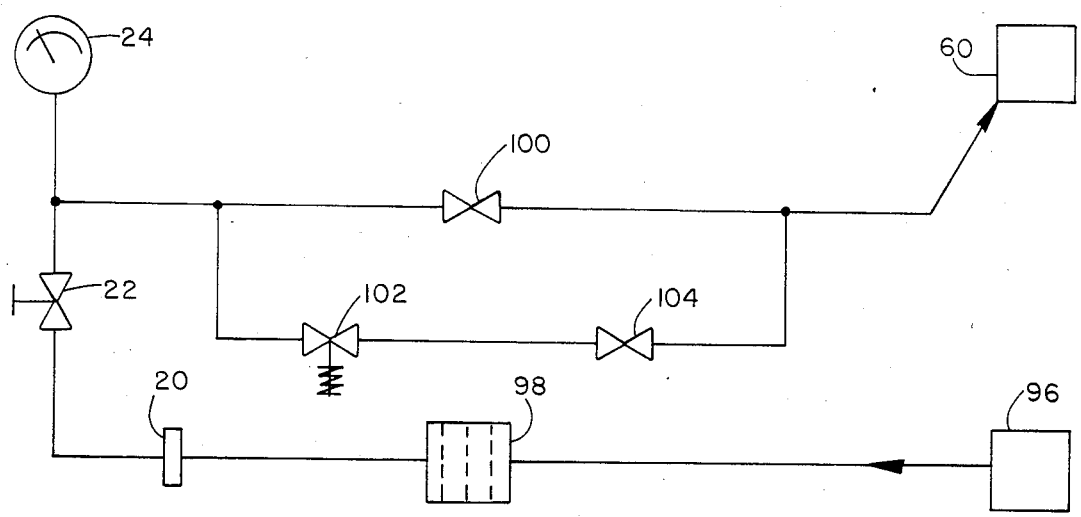
FIG. 2 is a schematic diagram of the oven gas flow system.

The purge gas supply system of the oven 10 is illustrated in FIG. 1 and FIG. 2. A supply 96 of inert or reactive purge gas is appropriately connected to the gas inlet orifice 40 located on the rear panel 12d of the oven 10. The purge gas is preferably an inert gas such as nitrogen, argon, or carbon dioxide and preferably has a density less than oxygen. The supply 96 may be a laboratory common supply (manifold nitrogen) or bottled nitrogen, as long as the supply 96 provides a constant or fixed purge gas pressure as registered on the gauge 24. The preselected purge gas entering the purge gas inlet orifice 40 initially passes through a filter 98, which catches any foreign material that might affect the subsequent control orifices. The purge gas thereafter flows to the dual function purge gas pressure switch 20. The pressure switch 20 functions both as a light to indicate there is at least some purge gas supply pressure and as a reset device, to prevent a test from being continued without the operator being aware of a gas failure. Purge gas thereafter flows through the ON/OFF purge gas valve 22 to the purge gas pressure gauge 24.

When the gas valve 22 is open and a supply 96 of purge gas is available, the gas pressure switch 20 will be lit and the gauge 24 will provide a positive reading. When the gas valve 22 is closed and a purge gas supply 96 is available, the gas pressure switch 20 will be lit but the pressure gauge 24 will provide a zero pressure reading. Therefore, when the value 22 is open, the preselected purge gas will continuously flow to the ante chamber 60 through a first internal orifice or needle valve 100. The gas valve 22 is thus used to conserve gas since low flow always occurs when it is open, even if the power switch 18 is OFF. Orifice 100 is preferably preset to provide a gas flow of approximately 150 cc/min when purge gas is supplied at a fixed pressure of approximately 20 psig.

The gas flow system, as illustrated in FIG. 2, is also provided with a solenoid 102 and a second internal orifice or needle valve 104. Orifice 104 is also preferably preset to provide an additional gas flow therethrough of approximately 450 cc/min when supply gas pressure is approximately 20 psig. Thus, when the gas valve 22 is open and the solenoid 102 is energized by the controller 16, the preselected gas will flow at a rate of approximately 600 cc/min when the gas supply pressure is approximately 20 psig. Of course, a higher purge gas pressure will give a proportionally higher flow rate. As a result, when the supply 96 is approximately 20 psig, the gas flow system of oven 10 is capable of providing either a low flow rate of approximately 150 cc/min or a high flow rate of approximately 600 cc/min, as determined by the controller 16 and the program selected by the oven operator.

Prior to the actual operation of the invention oven 10, the power supply line 36 will be connected to an appropriate power supply, depending upon the particular electrical option of the oven 10. The ON/OFF power switch 18 is thereafter utilized to provide power between the power supply line 36 and the controller 16, heater elements 66, fan 94, and other components of the oven 10. The power switch 18 will preferably be lit when power is being supplied to the various components of the oven 10.

To operate the invention oven 10, a liquid or solid material 105, such as a petroleum product or other distillable material, is preferably placed within one or more glass vials 106 which are supported by an aluminum sample basket 108, as illustrated in FIG. 9. The utilization of an aluminum basket helps to distribute the heat evenly to the samples 105. The basket 108 is then placed within the inner heating chamber 48 through opening 50 and received therein or supported by bottom floor 49. It is to be understood that the test material 105 will preferably be weighed before it is introduced to the oven 10 and that the use of a plurality of glass vials 106 permits the controlled heating of more than one different test material during a single test. Furthermore, it is essential to the proper operation of the oven 10 that the basket 108 not restrict the gas outlet port 52. As such, it is preferable that the basket 108 be provided with a pair of centrally aligned ports 109 which permit the outward flow of purged gas through outlet port 52. It is also preferable that the basket 108 be centered within inner heating chamber 48 so as not to touch the tip of the thermocouple 69 or the inner wall 48a. Proper centering of basket 108 also assures a uniform temperature profile for heating the material 105.

After the test material 105 has been introduced to the oven 10, the gravity lid 26 is removed from lid rest 30 and lowered gently onto the top of inner heating chamber 48 by means of handle 28. Lid 26 thereby seals the top opening 50 of inner heating chamber 48 by the mating of spherical bottom 41 or spherical seal 46 with the chamfered edge 54 and the downward pull of gravity on the lid 26. Thus, the gravity seal lid 26 provides an effective seal for inner heating chamber 48 and prohibits the introduction of ambient air thereto or the loss of purge gas therefrom during the operation of the oven 10. Furthermore, the simple, gravity seal lid 26 can be readily removed from inner chamber 48 and does not create a bomb by being firmly secured thereto. That is, the lid 26 will be urged open if pressure build-up within inner chamber 48 exceeds safe limits.

It is to be understood that the heating chamber 48 will initially be filled with oxygen and the other elements of the ambient air after the material 105 is introduced thereto and sealed therein. Nevertheless, the air will initially be purged from inner heating chamber 48 by the preselected purge gas from supply 96 prior to initiating the actual heating phase of the oven 10. When the gas valve 22 is open and a preselected purge gas, such as nitrogen, is available and being supplied to the system through appropriate gas tubing 99, the gas pressure switch 20 will be lit, the pressure gauge 24 will register the purge gas pressure from supply 96, and internal orifice 100 will permit a low flow of purge gas to the ante chamber 60 through gas feed line 64. Furthermore, when the solenoid 102 is energized by the controller 16, the pressure reading of gauge 24 will remain substantially unchanged, but first internal orifice 100 and second internal orifice 104 will combine to permit a high flow of purge gas to the ante chamber 60 through gas feed line 64.

Figure 11:
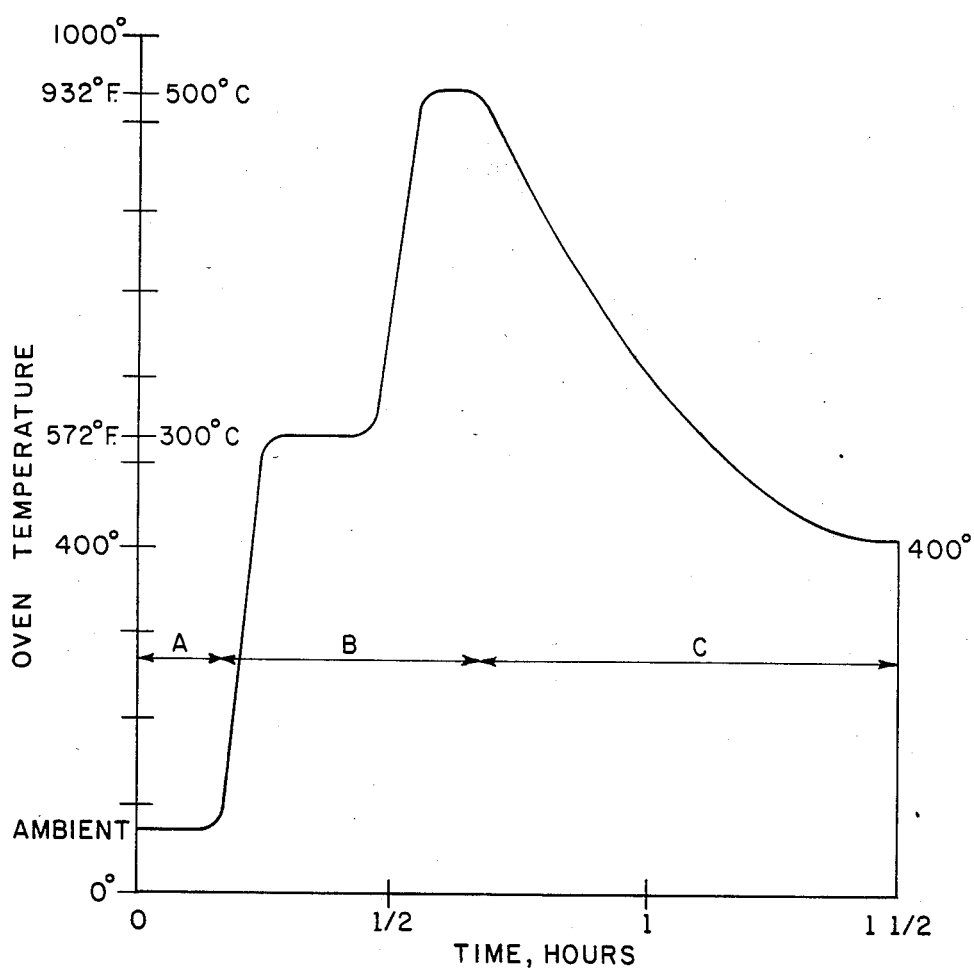
FIG. 11 is a graph illustrating a typical time and temperature process utilized in the invention oven.

Prior to the initiation of the heating phase, the controller 16 will be pre-programmed to permit the controlled heating of the test material 105 at the rate and temperature desired. Use of the invention oven 10 to determine percentage carbon residue of a material sample of approximately 1 gram requires a time and temperature process that closely approximates the actual path of the standard CCR test. As illustrated in FIG. 11, the basic process steps include a purge of the inner heating chamber for approximately 10 minutes (STEP A), a two step heat cycle for approximately 30 minutes (STEP B), and a cooling period for approximately 45 minutes (STEP C). It is to be understood that the use of a programmable controller 16, such as the Barber-Coleman Model 570, permits a desired ramping or temperature change over a preselected time period at a preselected rate, as well as a desired soak or constant temperature over a preselected time period. The controller 16 also specifies the purge gas flow at each step and is able to hold the selected sequence in memory for use at any time. Since the controller 16 does not control low gas flow, it monitors gas flow by controlling the solenoid 102. As a result, the controller 16 is able to monitor the entire testing procedure without further intervention by the operator.

During the initial purging phase or STEP A, the preselected purge gas enters the ante chamber 60 and passes therefrom into the outer gas flow chamber 58 through opening 61. The purge gas continues to flow through outer gas flow chamber 58 into the top of inner heating chamber 48 through purge gas inlet ports 51, as illustrated by the arrows in FIG. 1. As it flows through the outer gas flow chamber 58, the purge gas flows around and continuously bathes the heater elements 66 therein. It is to be understood that the preferably lighter purge gas entering the top of inner heating chamber 48 will gradually displace the denser air therein by urging its outward through gas outlet port 52. In contrast to other ovens wherein purging is achieved by the forceful flow of purge gas therethrough, the invention oven 10 uses density differential to an advantage. The displaced or purged air is thereafter drawn out of the oven 10 through gas exhaust tube 62 and the gas exhaust chimney 42, which is connected to the gas exhaust tube 62 intermediate to the ante chamber 60 and condensate trap 34. At the conclusion of STEP A, the inner heating chamber 48 will be substantially purged of oxygen and filled with the preselected purge gas at ambient pressure.

During the heating phase or STEP B, the resistance heater elements 66 are continuously monitored by the controller 16 and thermocouple 69, the cooperation therebetween achieving the desired temperature profile within the inner heating chamber 48. Surrounding the outer wall 48b with the heater elements 66 further assists in the creation of a uniform temperature profile within inner heating chamber 48. The use of a round or cylindrical inner heating chamber 48 also permits the test material 105 to be thoroughly and evenly heated. It is to be understood that the heater elements 66 will heat the walls 48a and 48b of inner heating chamber 48 by conduction and that the inner wall 48a will thereafter heat the material 105 by convection and radiation, as illustrated by the crooked arrows in FIG. 1. The temperature during a constant or soak period is close to that of the chamber wall 48a which radiates to the contents of the chamber 48 and maintains a uniform temperature. The temperature during a change or ramp may be increased at a very low rate, say 1° C. or less per minute, or a high rate up to nearly 50° C. per minute. It is also to be understood that the controller 16 may be pre-programmed for either a Celsius or Fahrenheit temperature scale and may be programmed to provide a temperature in excess of 600° C. within the inner heating chamber 48.

As illustrated in FIG. 5, the thermocouple 69 is preferably placed so that it protrudes through the inner wall 48a into the inner heating chamber 48 so that the tip of the thermocouple 69 becomes part of the inner wall 48a. Process temperature on the controller 16 is the temperature of the thermocouple 69. At times of increasing temperature, the wall 48a will slightly lead the thermocouple 69 and gas temperature by an amount that depends on the rate of temperature increase. Gradual or restricted output ramping is used to minimize these potential temperature differences throughout the oven. During soak periods, all temperatures will eventually be very close, because the temperatures of all surfaces will become that of the heat source (the wall 48a) as it radiates inward to objects in the oven. In the heating process, gases gain heat predominantly by conduction, whereas solids and liquids are heated predominantly by radiation; very little heating occurs by convection. During cooling, temperatures will be close, but the wall 48a will be ahead in the cooling rate unless a down ramp is followed.

Spherical bottom 41 and spherical seal 46 are preferably insulated to help maintain a high inside surface temperature and thereby prevent condensation thereon. As illustrated in FIG. 1, the bottom 41 and seal 46 may also be provided with a point or tip 47 to further assist in the removal of condensate therefrom. Condensate forming on bottom 41 or seal 46 will naturally collect at point 47 and fall therefrom through the gas outlet port 52 and the gas exhaust tube 62 located immediately therebelow. The aligned ports 109 in the center of the basket 108 permit the passage of condensate therethrough into the trap 34, thereby prohibiting the reintroduction of the condensed material to the glass vials 106.

Throughout the heating phase, the heated distillable material 105 will emit a volatile gas or vapor within the inner heating chamber 48. Nevertheless, the denser volatile gas will be continuously displaced from the inner heating chamber 48 through gas outlet port 52 by the continuous flow of lighter purge gas through gas inlet ports 51, as illustrated by the arrows in FIG. 1. Thus, the toxic and potentially explosive material gas will not collect within inner heating chamber 48. It is to be understood, however, that during the heating process, the preselected purge gas entering the inner heating chamber 48 will be much warmer than the purge gas entering the ante chamber 60. This is due to the continuous flow of cooler purge gas from ante chamber 60 around the heater elements 66 within the outer gas flow chamber 58.

As the denser material gas is displaced from inner heating chamber 48 through gas outlet port 52, it is condensed within gas exhaust tube 62 and collected in condensate trap 34. Condensation is accomplished by the introduction of the cooler purge gas into the ante chamber 60 which surrounds the upper portion of gas exhaust tube 62. The hot material vapor purged from inner heating chamber 48 is thus cooled and thereby condensed within the gas exhaust tube 62. The small amount of volatile material gas which does not condense is permitted to flow outward therefrom through the exhaust chimney 42 connected between the gas exhaust tube 62 and an exhaust hood (not shown). A line from the exhaust hood is preferably placed within a few centimeters of the exhaust chimney 42 so that rising gas is caught entirely and removed without creating any actual suction on the chimney 42. Thus, the invention oven 10 is able to reduce the amount of toxic gas exhausted to the atmosphere and provide for proper disposal of the toxic condensate within trap 34.

It is to be understood that the presence of the concealed heater elements 66 within the outer gas flow chamber 58 and the continuous bathing thereof by the purge gas as it flows therethrough protects the heater elements 66 from deterioration and corrosion due to the volatile material vapor. Furthermore, the continuous purging of the volatile gas from inner heating chamber 48 reduces the likelihood of a fire or explosion due to its collection therein. The preselected purge gas thus provides an explosion safe heating chamber 48 while at the same time contributing to the life expectancy of the heater elements 66. The likelihood of an explosion is further reduced by the utilization of a gravity seal lid 26, which will be forced off if the pressure within chamber 48 becomes too great. Such a lid design thus eliminates a pressure build-up that could lead to a potential explosion. Finally, it is to be understood that either the low or high gas purging rate can be utilized during any phase of the operation of the oven 10 as selected by the oven operator and programmed into the controller 16.

Throughout the heating phase, the sensitive controller 16 will be continuously protected from the high temperature within test chamber 11 by the thermal barrier 86 within cabinet 12 and the continuous flow of ambient air into the control chamber 13 through inlet ports 92. The control chamber cooling air is thereafter urged outward through control chamber outlet ports 32 by exhaust fan 94. The test chamber 11 of oven 10 is also kept relatively cool by the insulation layers 74, 76, and 80 and by the continuous flow of ambient air through inlet ports 84 and outlet ports 44.

If the gas supply 96 falls below a preset pressure level during operation of the oven 10, a pressure sensor will sense low pressure and simultaneously cause the gas switch light 20 to go out and the controller 16 to go into a remote-hold mode. The controller program will not continue until gas pressure is resumed and the gas pressure switch 20 is pushed and held, thereby releasing the remote-hold relay. This internally wired feature prevents a test from being continued without the operator being aware of the gas supply being depleted. Normally such a faulted test would be discarded since consistent gas flow is important to eliminate oxygen and maintain the basic conditions of the test.

During the cooling phase or STEP C, the controller 16 will cease the flow of power through resistance heater elements 66 and preferably energize solenoid 102. The energized solenoid 102 (which may also be set externally) permits the additional flow of purge gas through second orifice 104, thereby providing a high gas flow to the inner heating chamber 48. The high flow of purge gas around the heater elements 66 within outer gas flow chamber 58 further assists in the cooling thereof. The purge gas in heat exchange relationship with the heater elements 66 and inner heating chamber 48 thus reduces the time required for cooling the oven 10.

At the conclusion of the cooling phase, the lid 26 can be removed from the inner heating chamber 48 and placed on the lid rest 30 for rapid cooling thereof by the fan 94. The basket 108 can thereafter be removed from the inner heating chamber 48 and the test material 105 can be reweighed to determine the weight loss of the material. The glass condensate trap 34 may also be unscrewed from the cap 35 for cleaning purposes and proper disposal of the condensed material therein. Once the inner heating chamber 48 has been sufficiently cooled and the condensate trap 34 has been resecured, the oven 10 is ready for the initiation of another test.

The invention oven 10 is thus able to utilize small test samples and duplicate the CCR test with improved precision, accuracy, reliability, and simplicity. However, although the invention oven 10 has been designed primarily for testing the coke forming tendency of petroleum products, it can also be used for destructive distillation, curing, roasting, drying, catalytic reaction, or any similar small scale batch heating of liquids or solids in an ambient pressure gas atmosphere. Furthermore, the controller 16 can be programmed to provide the desired temperature and gas flow profile within the inner heating chamber 48 as dictated by the particular batch heating process utilized.

In the preferred embodiment, the cabinet 12 has a width of approximately sixteen inches, a depth of approximately fourteen inches, and a height of approximately thirteen inches (including approximately three inches for legs 14). The cabinet 12, lid 26, and chambers 48, 58 are preferably constructed of stainless steel. The gas supply system is preferably constructed of stainless steel and brass tubing. Finally, the appropriate metal components of the oven 10, which are connected are preferably welded together, thereby eliminating the need for elaborate forming or casting.

While the invention controlled atmosphere oven has been described in connection with the preferred embodiment, it is not intended to limit the invention to the particular form set forth, but on the contrary, it is intended to cover such alternatives, modifications, and equivalents as may be included within the spirit and scope of the invention as defined by the appended claims.

I claim:

1. An oven for heating a material in a preselected gas atmosphere, comprising:
    a first chamber normally having a first gas therein, said first chamber having an opening for receiving said material therethrough and being adapted to receive said material therein;
    means for sealing said opening in said first chamber after said material is received therethrough;
    a second chamber surrounding said first chamber, said second chamber being adapted to receive said preselected gas therein and said first chamber having at least one gas inlet port therethrough to permit said preselected gas to flow from said second chamber into said first chamber;
    heating means located within said second chamber for heating said first chamber, thereby to heat said material therein;
    means for introducing said preselected gas to said second chamber to thereby displace said first gas from said first chamber, said first chamber having a gas outlet port therethrough to permit said first gas to flow outward therefrom during said displacement thereof by said preselected gas; and
    first gas receiving means connected to said first chamber for receiving said first gas during said displacement thereof by said preselected gas, said gas outlet port permitting communication between said first chamber and said first gas receiving means, wherein said second chamber comprises an outer chamber and an ante chamber in communication therewith, and wherein said preselected gas is introduced to said ante chamber and said ante chamber surrounds said first gas receiving means, sdaid preselected gas within said ante chamber causing said first gas to condense within said first gas receiving means.

2. An oven for heating a material in a preselected gas atmosphere, as recited in claim 1, further comprising means for collecting said condensed gas located at a termination of said first gas receiving means.

3. An oven for heating a material in a preselected gas atmosphere, as recited in claim 1, wherein said means for sealing said opening in said first chamber comprises a floating spherical seal and wherein said first chamber has a chamfered edge for receiving said seal.

4. An oven for heating a material in a preselected gas atmosphere, as recited in claim 1, wherein said first gas receiving means comprises a gas exhaust tube.

5. An oven for heating a material in a preselected gas atmosphere, comprising:
    an inner chamber normally having a first gas therein, said inner chamber having an opening for receiving said material therethrough and being adapted to receive said material therein;
    means for sealing said opening in said inner chamber after said material is received therethrough;
    a second chamber surrounding said inner chamber, said second chamber comprising an outer chamber and an ante chamber in communication therewith, said second chamber being adapted to receive said preselected gas therein and said inner chamber having a plurality of gas inlet ports therethrough near said opening to permit said preselected gas to flow from said second chamber into said inner chamber;
    heating means located within said outer contiguous to an outer wall of said inner chamber, thereby to heat said inner chamber and said material therein;
    means for introducing said preselected gas to said ante chamber, thereby to displace said first gas from said inner chamber;
    first gas receiving means surrounded by said ante chamber for receiving said first gas from said inner chamber, said inner chamber being adapted to permit said first gas to be received by said first gas receiving means during said displacement thereof by said preselected gas, said preselected gas within said ante chamber causing said first gas to condense within said first gas receiving means; and
    means for collecting said condensed gas located at a termination of said first gas receiving means.

6. An oven for heating a material in a preselected gas atmosphere, as recited in claim 5, wherein said means for sealing said opening in said inner chamber comprises a floating spherical seal and wherein said inner chamber has a chamfered edge for receiving said seal.

7. An oven for heating a material in a preselected gas atmosphere, as recited in claim 5, wherein said means for introducing said preselected gas comprises a gas feed line in communication with said ante chamber.

8. An oven for heating a material in a preselected gas atmosphere, as recited in claim 5, wherein said first gas receiving means comprises a gas exhaust tube.

9. An oven for heating a material in a preselected gas atmosphere, as recited in claim 5, wherein said means for collecting said condensed gas comprises a condensate trap.

10. A method for heating a distillable petroleum material contained within a receptacle in a preselected gas atmopshere, comprising the steps of:

(a) introducing said receptacle to a first chamber having a first gas therein, said first chamber having an opening therethrough and being adapted to receive said receptacle therein;

(b) sealing said opening in said first chamber;

(c) introducing said preselected gas to a second chamber surrounding said first chamber in communication therewith, said second chamber having means for heating said first chamber located therein contiguous to a wall of said first chamber, said wall of said first chamber intermediate said heating means and said receptacle, said first chamber having a plurality of gas inlet ports therethrough near said opening to permit said preselected gas to flow from said second chamber into a top of said first chamber, thereby to displace said first gas through a bottom of said first chamber, said first chamber permitting said first gas to flow outward therefrom upon said displacement thereof by said preselected gas; and (d) heating said first chamber at a rate and temperature desired, thereby heating said material within said receptacle.

11. A method for heating a distillable petroleum material contained within a receptacle in a preselected gas atmosphere, as recited in claim 10, comprising the additional steps of condensing said first gas and collecting said condensed first gas for subsequent disposal thereof.

12. A method for heating a distillable petroleum material contained within a receptacle in a preselected gas atmosphere, as recited in claim 10, comprising the additional steps of weighing said material prior to introducing said receptacle to said first chamber, removing said receptacle from said first chamber after said heating step, and reweighing said material after said step of removing said receptacle from said first chamber.

* * * * *